United States Patent [19]
Le Royer et al.

[11] Patent Number: 5,939,079
[45] Date of Patent: Aug. 17, 1999

[54] PROCESS FOR THE DISPERSION BY HIGH-PRESSURE HOMOGENIZATION OF PULVERULENT FILLERS IN A VEHICLE COMPOSED OF AT LEAST ONE FATTY PHASE, COMPOSITIONS OBTAINED AND USES

[75] Inventors: Isabelle Le Royer, Jouy en Josas; Catherine Thibaut, Paris, both of France

[73] Assignee: L'Oreal, Paris, France

[21] Appl. No.: 08/778,348

[22] Filed: Jan. 3, 1997

[30] Foreign Application Priority Data

Jan. 3, 1996 [FR] France ................................ 96 00029

[51] Int. Cl.$^6$ ............................ A61K 7/02; A61K 7/021; A61K 7/04; A61K 7/035
[52] U.S. Cl. ............................. 424/401; 424/61; 424/69; 424/70.1; 424/70.7; 514/844; 514/845; 514/846; 514/937; 106/436; 106/437
[58] Field of Search ................................ 424/401, 61, 69, 424/70.1, 70.7; 514/844, 845, 846, 937; 106/436, 437

[56] References Cited

U.S. PATENT DOCUMENTS

| | | | |
|---|---|---|---|
| 5,610,201 | 3/1997 | Grollier et al. | 514/773 |
| 5,741,518 | 4/1998 | Ribier et al. | 424/450 |

FOREIGN PATENT DOCUMENTS

| | | | |
|---|---|---|---|
| 0 581 651 A2 | 2/1994 | European Pat. Off. | C09C 1/00 |
| A-59-084938 | 5/1984 | Japan . | |
| A-59-086640 | 5/1984 | Japan . | |
| A59-091123 | 5/1984 | Japan . | |
| A-1051128 | 2/1989 | Japan . | |
| A-1050985 | 12/1966 | United Kingdom . | |
| WO-A-9505144 | 2/1995 | WIPO . | |
| WO-A-9614925 | 5/1996 | WIPO . | |

OTHER PUBLICATIONS

"Makeup Formulary", cosmetics and Toiletries, vol. 104, pp. 67–103, Jul. 1989.
fox, C., "Advances in Cosmetic Science and Technology, I. Pigments and Makeup", Cosmetics and Toiletries, vol. 109, pp. 39–51, Apr. 1994.
English Language Derwent Abstract of WO–A–9505144.
English Language Derwent Abstract of JP–A–59091123.
English Language Derwent Abstract of JP–A–1051128.
English Language Derwent Abstract of JP–A–59086640.

*Primary Examiner*—Donna C. Wortman
*Assistant Examiner*—Brenda G. Brumback
*Attorney, Agent, or Firm*—Finnegan, Henderson, Farabow, Garrett & Dunner, L.L.P.

[57] ABSTRACT

The present invention relates to a process for the dispersion of at least one pulverulent organic filler and/or of at least one pulverulent inorganic filler in a vehicle composed of at least one fatty phase, by mixing the filler or fillers in the vehicle by high-pressure homogenization in one or a number of passes, to the cosmetic or dermatological compositions capable of being obtained by this process. The present invention also relates to the use of the compositions obtained by this process as the basis for care, make-up and/or hygiene products. The present invention also relates to the use of the compositions obtained by this process as the basis for products for protecting the skin, hair, scalp, nails, eyelashes, eyebrows and/or mucous membranes against the effects of ultraviolet radiation.

60 Claims, No Drawings

PROCESS FOR THE DISPERSION BY HIGH-PRESSURE HOMOGENIZATION OF PULVERULENT FILLERS IN A VEHICLE COMPOSED OF AT LEAST ONE FATTY PHASE, COMPOSITIONS OBTAINED AND USES

The present invention relates to a process for the dispersion of at least one pulverulent organic filler and/or of at least one pulverulent inorganic filler in a vehicle composed of at least one fatty phase. The process comprises at least one stage of mixing the filler or fillers in the vehicle by high-pressure homogenization in one or a number of passes. The present invention also relates to the cosmetic or dermatological compositions capable of being obtained by this process.

It is well known that light radiation with wavelengths of between 280 nm and 400 nm makes it possible for the human skin to tan and that radiation with a wavelength of between 280 and 320 nm, known under the name of UV-B, causes erythemas and skin burns which can harm the development of natural bronzing. This UV-B radiation must therefore be screened.

It is also known that UV-A radiation, with wavelengths of between 320 and 400 nm, which causes the skin to tan, is capable of leading to a detrimental change in the latter, especially in the case of sensitive skin or skin which is continually exposed to solar radiation. In particular, UV-A radiation causes a loss of skin elasticity and the appearance of wrinkles leading to premature ageing. It promotes the triggering of the erythemal reaction or accentuates this reaction in certain subjects and can even be the cause of phototoxic or photoallergic reactions. It is therefore desirable to screen the UV-A radiation as well.

Many compositions intended for the photoprotection (UV-A and/or UV-B) of the skin and/or the scalp have been proposed to date. In this field, it is observed that the use of inorganic nanopigments, i.e., pigments in which the mean size of the primary particles does not generally exceed 100 nm, based on metal oxides, and in particular on titanium oxide, is becoming increasingly frequent. The popularity of inorganic nanopigments is due to the fact that when they are used in combination with conventional UV screening agents (mainly organic compounds capable of absorbing harmful radiation) it is possible to obtain very high protection factors.

For various reasons relating in particular to better smoothness, emollience and general comfort of use, current photoprotective compositions are most often provided in the form of a dispersion. The dispersion can be of oil-in-water type, i.e., a vehicle composed of a continuous dispersing aqueous phase and of a non-continuous dispersed oily phase or of water-in-oil type, i.e., a vehicle composed of a continuous dispersing fatty phase and of a non-continuous dispersed aqueous phase. The abovementioned nanopigments have been introduced into these dispersions at various concentrations and, if appropriate in combination with other conventional UV screening agents. The nanopigments may be present in both the aqueous phase of the dispersion and in its oily phase (also known as the fatty phase).

One of the major disadvantages of the compositions known to date and belonging to the above type and more particularly of those containing titanium oxide ($TiO_2$) nanopigments is that, once applied to the skin in the form of a film, they bring about a whitening effect and a rough feel on the skin which are cosmetically undesirable and generally little appreciated by the users. These effects are essentially due to the presence of more or less large aggregates formed by the nanopigments generally in the powder form.

Moreover, another difficulty lies in the fact that conventional oil-in-water or water-in-oil dispersions based on protective nanopigments result, after application to the skin, in an uneven, non-homogeneous, indeed crude, distribution of the said nanopigments on this skin, which can harm the quality of the overall photoprotective effect desired. This poor distribution of the nanopigments which is observed at the surface of the skin is often related to the fact that even the initial dispersion (before application) is substantially non-homogeneous, i.e., poor dispersion of the pigment in its vehicle.

The present inventors have discovered, in a surprising way, a new process for the dispersion of pulverulent organic fillers and/or of pulverulent inorganic fillers in a vehicle composed of at least one fatty phase which makes it possible to obtain new dispersions of these pulverulent fillers which are substantially finer and more homogeneous than the formulations of the same type obtained by conventional means for dispersing fillers, such as stirring by shearing with a device of the Moritz type.

In particular, oil-in-water or water-in-oil dispersions containing, as pulverulent fillers, inorganic nanopigments based on metal oxides obtained according to the process of the invention can constitute new cosmetic or dermatological compositions which do not result in whitening phenomena on the skin on application or which at least result in a significantly reduced whitening effect. In addition, they exhibit substantially improved cosmetic properties, in particular as regards smoothness to the touch with respect to conventional oil-in-water or water-in-oil dispersions.

The process in accordance with the present invention is a process for the dispersion of at least one pulverulent organic filler and/or of at least one pulverulent inorganic filler in a vehicle comprising at least one fatty phase, where the process comprises at least one stage of mixing the filler or fillers in the vehicle by high-pressure homogenization. Preferably, the homogenization is carried out in a high-pressure homogenization device in one or a number of passes.

The high-pressure homogenization devices used according to the invention are selected in particular from those of the RANNIE®, GAULIN®, or SOAVIE® type.

The pressures used preferably vary from 100 to 800 bars (from 1 to $8 \times 10^7$ Pa) and more particularly from 200 to 500 bars (from 2 to $5 \times 10^7$ Pa).

The homogenization temperature used preferably varies from 20 to 85° C. and more particularly from 25 to 70° C.

The vehicle can be composed of a single fatty phase in which the pulverulent fillers are dispersed. The choice will preferably be made of a fatty phase generally composed of one or a number of cosmetically or dermatologically acceptable compounds selected, alone or as mixtures, from the various fatty substances, oils of vegetable, animal or mineral origin, natural or synthetic waxes, and the like.

The vehicles which are particularly sought after in the context of the process of the invention are oil-in-water or water-in-oil dispersions composed of a fatty phase and of an aqueous phase, such as those indicated above.

In the context of oil-in-water or water-in-oil dispersions, an alternative form of the process in accordance with the invention comprises the predispersion of the filler or fillers in a portion of the fatty phase of the oil-in-water or water-in-oil dispersion using the high-pressure homogenizer and then the remixing of the mixture thus obtained with the entire amount of the fatty phase before the final mixing with the aqueous phase.

In the context of oil-in-water or water-in-oil dispersions, a second alternative form of the process in accordance with the invention comprises the predispersion of the filler or fillers in the fatty phase of the oil-in-water or water-in-oil dispersion using the high-pressure homogenizer before the final mixing with the aqueous phase.

In the context of oil-in-water or water-in-oil dispersions, a third alternative form of the process in accordance with the invention comprises the mixing of the filler or fillers in the oil-in-water or water-in-oil dispersion produced beforehand using the high-pressure homogenizer.

According to each of these three alternative forms, the final stage of mixing in the aqueous phase or the stage of prior production of the oil-in-water or water-in-oil dispersion can be carried out using the high-pressure homogenizer or conventional stirring means, such as a device of the Moritz type.

Another subject of the invention comprises a cosmetic or dermatological composition in the form of a dispersion of at least one organic filler and/or one inorganic filler in a vehicle composed of at least one fatty phase, characterized in that it is capable of being obtained according to the dispersing process as described above.

The cosmetic or dermatological compositions according to the invention are preferably water-in-oil or oil-in-water dispersions and more preferably water-in-oil or oil-in-water emulsions. The latter are more preferably used. Indeed, for cosmetic reasons and reasons of comfort of use, oil-in-water emulsions are the ones which are in greatest demand in the field of cosmetics, due to the fact that they contribute to the skin, on application, a smoother, less greasy and lighter feel than water-in-oil dispersion systems.

The fillers used in the compositions of the invention are cosmetic or dermatological particles which are insoluble in the medium of the composition.

The fillers used according to the invention can be selected from inorganic or organic fillers of lamellar or spherical structure or their mixtures. They may be compactable or difficult to compact. A filler which is difficult to compact is understood to mean a raw material which, beyond a certain percentage which will depend on the material in question, cannot be compacted by means of a mechanical press.

Each type of filler makes it possible to introduce specific and different qualities into the composition according to the invention. Thus, for example, fillers of lamellar inorganic type generally introduce smoothness, fillers of spherical inorganic type generally introduce good disintegration and spherical organic fillers generally have a structuring role and introduce smoothness.

Mention may preferably be made, among fillers of lamellar inorganic type, of:

talcs or hydrated magnesium silicates in the form of particles with sizes generally of less than 40 µm;

micas or aluminosilicates of varied compositions and which exist in the form of flakes having sizes of 2 to 200 µm, preferably 5–70 µm, and a thickness of 0.1 to 5 µm, preferably of 0.2–3 µm, it being possible for these micas to be of natural origin, for example muscovite, margarite, roscoelite, lepidolite or biotite or of synthetic origin, the micas or aluminosilicates are generally transparent and make it possible to confer a satin appearance on the skin;

clays, such as sericites, which belong to the same chemical and crystalline class as muscovite but which possess organoleptic properties similar to those of talc;

kaolin or hydrated aluminium silicate, which exists in the form of particles of isotropic shapes having sizes generally of less than 30 µm and which possess good absorption properties with respect to fatty substances; and boron nitrides.

These fillers are generally compactable.

However, among these fillers of lamellar inorganic type, some are difficult to compact. Mention may thus preferably be made of:

some talcs, such as "TALC K1" from Nippon or "TALC EXTRA STEAMIC OOS" from Luzenac;

some sericites, such as "SERICITE BC282" from Whittaker; and the majority of titanium oxide-coated micas, when they are used at a high percentage, among which mention may preferably be made of the titanium nanooxide-coated mica "COVERLEAF PC 2055M" from Ikeda.

Mention may preferably be made, among compactable fillers of lamellar organic type, of tetrafluoroethylene polymer powders, such as "FLUON" from Montefluos or "HOSTAFLONQ" from Hoechst AG.

Mention may preferably be made, among fillers of lamellar organic type which are difficult to compact, of the lauroyllysine "AMINHOPE LL-11" from Ajinomoto.

Mention may preferably be made, among compactable fillers of spherical inorganic type, of:

zinc and titanium oxides, generally used in the form of particles having sizes not exceeding a few micrometers (or even less than 1 µm in the case of titanium oxide), in particular spherical titanium dioxides, such as "SPHERITITAN" from Ikeda; these oxides have an oily feel, a good covering power and a high opacity;

precipitated calcium carbonate which, in the form of particles with sizes greater than 10 µm, has an oily feel and makes it possible to obtain a matt appearance;

magnesium carbonate and hydrogencarbonate which possess in particular fixing properties with respect to fragrances;

non-porous spherical silica and hydroxyapatite.

Mention may preferably be made, among fillers of spherical inorganic type which are difficult to compact, of:

silica microspheres with an open porosity or, preferably, hollow silica microspheres, such as "SILICA BEADS" from Maprecos, these microspheres advantageously being impregnated with a cosmetic active principle; and "MACROLITE" glass or ceramic microcapsules from 3M.

Mention may preferably be made, among compactable fillers of spherical organic type, of:

metal soaps derived from organic carboxylic acids having from 8 to 22 carbon atoms, preferably from 12 to 18 carbon atoms, for example zinc, magnesium or lithium stearate, zinc laurate or magnesium myristate; these soaps, generally present in the form of particles having sizes of less than 10 µm, have an oily feel and facilitate the adhesion of the powder to the skin;

powders of non-expanded synthetic polymers, such as polyethylene, polyesters, for example polyethylene isophthalate or terephthalate and polyamides, for example, nylon, in the form of particles having sizes of less than 50 µm, which possess absorbent properties and make it possible to confer a velvety appearance on the skin;

spheronized powders of crosslinked or non-crosslinked synthetic polymers, such as powders of polyacrylic or polymethacrylic acid, powders of polystyrene crosslinked by divinylbenzene and powders of silicone resin; and powders of organic materials of natural origin, such as the starch octenylsuccinate sold under the name "DRY FLOW PLUS" by Amylum.

Mention may preferably be made, among fillers of spherical organic type which are difficult to compact, of:

microporous polymer microspheres which have a structure analogous to that of a sponge; they generally have a specific surface of at least 0.5 m$^2$/g, and in particular of at least 1 m$^2$/g, the said specific surface having no upper limit other than that resulting from the practical possibility of producing microspheres of very high porosity: the specific surface can, for example, reach 1,000 m$^2$/g or even more; and polymer microcapsules which contain a single closed cavity and form a reservoir which can contain a liquid, preferably a cosmetic active principle; they are prepared by known processes, such as those described in U.S. Pat. No. 3,615,972 and European Patent EP-A-056,219, the disclosures of which are hereby incorporated by reference.

With respect to the microporous polymer microspheres mention may preferably be made of acrylic polymer microspheres, such as those made of crosslinked acrylate copolymer "POLYTRAP" from Dow Corning and those of "MICROPEARL M" or "MICROPEARL M 100" poly (methyl methacrylate) from Seppic. These microporous microspheres can advantageously be impregnated, preferably with cosmetic active principles. Mention may preferably be made, in this respect, of the styrene-divinylbenzene copolymer microspheres sold under the trade name "PLASTIC POWDER FPSQ" by Toshiki, which are impregnated with squalene, which is an emollient cosmetic active principle.

The polymer microcapsules mentioned above can be prepared, for example, from polymers or copolymers of acid, amine or ester monomers containing ethylenic unsaturation, from urea-formaldehyde polymers or from polymers or copolymers of vinylidene chloride. Mention may preferably be made, by way of example, of microcapsules made from polymers of copolymers of methyl acrylate or methacrylate or alternatively from copolymers of vinylidene chloride and of acrylonitrile. Among the latter, those which contain, by weight, 20–60% of units derived from vinylidene chloride, 20–60% by weight of units derived from acrylonitrile and 0–40% by weight of other units, such as units derived from an acrylic and/or styrene monomer, will in particular be indicated. Use may also preferably be made of acrylic polymers or copolymers crosslinked, for example in the case of polymers containing a carboxyl group, by diols acting as crosslinking agents. Mention may preferably be made, by way of example, of the "EXPANCEL" microcapsules, made of vinylidene chloride-acrylonitrile copolymer, from Casco Nobel, the "Q-MAX" microcapsules from Q-Max and the "3 M" microcapsules from 3M.

The fillers dispersed according to the process in accordance with the invention can be organic pigments, inorganic pigments, which are coated or non-coated, or nacreous pigments or their mixtures.

Mention may preferably be made, among organic pigments, of lakes, such as D & C Red No. 7 calcium lakes, D & C Red No. 6 and 9 barium lakes, D & C Red No. 3 and D & C Yellow No. 5 aluminium lakes and D & C Orange No. 5 zirconium lakes.

Mention may preferably be made, among inorganic pigments, of iron oxides (red, brown, black and yellow), chromium oxides, ultramarines (aluminosilicate polysulphides), manganese pyrophosphate and Prussian blue (ferric ferrocyanide), or titanium oxides.

The nacreous pigments are preferably selected from white nacreous pigments, such as mica covered with titanium oxide or bismuth oxychloride, or coloured nacreous pigments, such as titanium oxide-coated mica with iron oxides, titanium oxide-coated mica with ferric blue or chromium oxide or titanium oxide-coated mica with an organic pigment of the abovementioned type, as well as pigments based on bismuth oxychloride.

The fillers used according to the invention are more preferably selected from inorganic nanopigments based on metal oxides which are coated or non-coated.

The metal oxides which can be used in the context of the present invention are preferably selected from titanium, zinc, iron, zirconium and cerium oxides or their mixtures. The mean size of the primary particles of these oxides preferably varies from 5 to 100 nm and more preferably from 10 to 50 nm.

Such coated or non-coated metal oxide nanopigments are products which are already well known to the person skilled in the art and are in particular described in European Patent Application EP-A-0,518,773, the disclosure of which is incorporated herein by reference. Mention may preferably be made, as commercial nanopigments which can be used in the context of the present invention, of the products sold under the trade names "UV-TITAN M 160,""UV-TITAN M 212," AND "UV-TITAN M 262" by Kemira and "MICROTITANIUM DIOXIDE-MT-100T" by Tayca.

According to a preferred embodiment of the cosmetic or dermatological compositions according to the invention, use is made of inorganic nanopigments based on titanium oxide which in fact are the most efficient with respect to photoprotection. This titanium oxide can exist in a crystalline form of rutile and/or anatase type and/or in an amorphous or substantially amorphous form. As indicated above, this pigment may then be coated or non-coated but use is preferably made of coated pigments, for example coated with alumina and/or aluminium stearate.

The fillers are present in the compositions of the invention in concentrations preferentially ranging from 0.1 to 70% by weight, depending on the application envisaged.

The nature of the fatty phase forming part of the composition according to the invention is not critical and it can thus comprise any compound which is already generally known as suitable for the manufacture of cosmetic dispersions of oil-in-water type or of water-in-oil type. In particular, these compounds can be selected, alone or as mixtures, from the various fatty substances, oils of vegetable, animal or mineral origin, natural or synthetic waxes, and the like.

Mention may preferably be made, among oils which can form part of the composition of the fatty phase, of:

mineral oils, such as liquid paraffin and liquid petrolatum;
oils of animal origin, such as perhydrosqualene;
oils of vegetable origin, such as sweet almond oil, avocado oil, castor oil, olive oil, jojoba oil, sesame oil, groundnut oil, grape seed soil, rapeseed oil, coconut oil, hazelnut oil, karite butter, palm oil, apricot kernel oil, calophyllum oil, rice bran oil, maize oil, wheat germ oil, soybean oil, sunflower oil, evening primrose oil, safflower oil, passion flower oil and rye oil; and
synthetic oils, such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and the esters derived from lanolic acid, such as isopropyl lanolate or isocetyl lanolate, isoparaffins and poly-α-olefins.

Mention may alternatively be made, as other oils which can be used in the emulsions according to the invention, of $C_{12}$–$C_{15}$ fatty alcohol benzoates ("FINSOLV TN" from Finetex), fatty alcohols, such as lauryl, cetyl, myristyl, stearyl, palmityl or oleyl alcohol, as well as 2-octyldodecanol, acetylglycerides, octanoates and decanoates of alcohols and of polyalcohols, such as those of glycol and of glycerol, ricinoleates of alcohols and of polyalcohols, such as those of cetyl, triglycerides of fatty acids, such as caprylic/capric triglycerides or triglycerides of saturated $C_{10}$–$C_{18}$ fatty acids, fluorinated and perfluorinated oils, lanolin, hydrogenated lanolin, acetylated lanolin and finally silicone oils, which may or may not be volatile.

Of course, the fatty phase can also contain one or a number of conventional lipophilic cosmetic adjuvants, in particular those which are already commonly used in the manufacture and the preparation of the compositions.

The aqueous phase can conventionally be composed of water or a mixture of water and polyhydric alcohol(s), such as, for example, glycerol, propylene glycol and sorbitol, or alternatively a mixture of water and water-soluble lower alcohol(s), such as ethanol, isopropanol or butanol (aqueous/alcoholic solution) and it can, of course, in addition contain conventional water-soluble cosmetic adjuvants.

Mention may preferably be made, among conventional cosmetic adjuvants capable of being contained in the aqueous phase and/or in the fatty phase of the dispersions in accordance with the invention (according to their water- and/or fat-soluble nature), of ionic or non-ionic thickeners, conventional hydrophilic or lipophilic organic sunscreening agents which are active in the UV-A and/or the UV-B, softeners, antioxidants, opacifiers, stabilizers, emollients, moisturizing agents, vitamins, fragrances, preservatives, sequestering agents, dyes, plasticizers or any other ingredient commonly used in the cosmetics field.

The compositions in accordance with the invention preferably contain, in addition, emulsifying surfactants for preparing and obtaining the dispersion. They can in addition contain coemulsifiers, the role of which, during the preparation of the dispersion, is substantially to decrease the amount of emulsifying surface-active agents used for preparing the dispersion.

The emulsifying systems which are suitable for the present invention can be emulsifiers of non-ionic type and can, more particularly still, be selected from polyoxyethylenated and/or polyoxypropylenated fatty alcohols, i.e., compounds obtained by reaction between an aliphatic fatty alcohol, such as behenyl alcohol or cetyl alcohol, and ethylene oxide or propylene oxide or an ethylene oxide/propylene oxide mixture and esters of fatty acids and of polyols, which are optionally polyoxyethylenated and/or polyoxypropylenated, i.e., compounds obtained by reaction of a fatty acid, such as stearic acid or oleic acid, with a polyol, such as, for example, an alkylene glycol or glycerol or a polyglycerol, optionally in the presence of ethylene oxide or propylene oxide or an ethylene oxide/propylene oxide mixture, or their mixtures. They are present in concentrations preferentially ranging from 0.5 to 40% by weight, preferably from 2 to 15% by weight, with respect to the total weight of the composition.

By way of indication,
the compositions in accordance with the invention in the form of a water-in-oil emulsion preferentially have the following formulations:

(i) aqueous phase: from 5 to 70% by weight, more particularly from 10 to 50% by weight, with respect to the whole formulation, (ii) fatty phase: from 30 to 95% by weight, more particularly from 40 to 85% by weight, with respect to the whole formulation, the compositions in accordance with the invention in the form of an oil-in-water emulsion preferentially have the following formulations:

(i) aqueous phase: from 5 to 95% by weight, more particularly from 10 to 85% by weight, with respect to the whole formulation, (ii) fatty phase: from 1 to 50% by weight, more particularly from 5 to 30% by weight, with respect to the whole formulation.

Another subject of the invention comprises the use of the compositions as defined above as the basis for a care, make-up and/or hygiene product.

Mention may preferably be made, among care compositions, of creams, milks, lotions or gels for caring for the body, the face, the hands or the lips.

Mention may preferably be made, among hygiene compositions, of make-up removers, shaving products, deodorants, or bath or shower creams, milks or gels.

Mention may preferably be made, among make-up compositions, of foundations, tinted creams, correctors, complexion enhancers, mascaras, eyeliners or lipsticks.

Another subject of the invention comprises the use of the compositions as defined above as the basis for a product for protecting the skin, hair, scalp, nails, eyelashes, eyebrows and/or mucous membranes against the effects of ultraviolet radiation, preferably anti-sun creams, milks or gels.

The products obtained from the compositions of the invention can be provided in the form of an oil-in-water or water-in-oil emulsion which is more or less thickened, of a gel, of a cream, of a milk, of a serum, of a lotion or of a product in the solid or pasty form.

The invention also relates to a process for the cosmetic treatment of the skin and/or scalp and/or nails and/or eyelashes and/or eyebrows and/or mucous membranes, where a composition as defined above is applied to the said substrates.

The invention also relates to a cosmetic treatment process for protecting the skin, scalp, nails, eyelashes, eyebrows and/or mucous membranes against the effects of ultraviolet radiation, characterized in that a composition as defined above is applied to the said substrates.

Of course, the person skilled in the art will take care to choose this or these possible additional compounds and/or their amounts so that the advantageous properties intrinsically attached to the composition in accordance with the invention are not, or not substantially, detrimentally affected by the envisaged addition or additions.

The examples below, given purely by way of illustration and without limitation, will make possible a better understanding of the invention.

EXAMPLES 1 TO 7

Oil-in-water Emulsions

The following Examples 1 to 7 were oil-in-water emulsions obtained according to the following procedure:

The inorganic nanopigments used in each example were incorporated in the fatty phase. The mixture was heated to 60–70° C. and was homogenized using a high-pressure homogenizer (500 bars pressure) of the Rannie type in one pass, and more if necessary. The emulsifying surfactants were added to the homogeneous mixture thus obtained. The aqueous phase was heated in parallel to the same temperature, the fatty phase/nanopigments/surfactants mixture was then incorporated in the aqueous phase and the emulsion was produced by stirring by shearing with a device of the Moritz type.

Example 1

Care Cream for the Skin

| Fatty phase | |
|---|---|
| Volatile silicone oil | 10.0 g |
| Liquid petrolatum | 5.0 g |
| Perhydrosqualene | 15.0 g |
| Emulsifying surfactants | 8 g |
| Cetyl alcohol | 1.2 g |
| Stearic acid | 0.1 g |
| Liquid lanolin | 4.0 g |
| Titanium oxide nanoparticles | 1.0 g |
| Aqueous phase | |
| Preservative | 0.3 g |
| Antioxidants | 0.1 g |
| Triethanolamine | 0.3 g |
| Demineralized water | q.s. for 100 g |

Example 2

Care Cream for the Skin

| Fatty phase | |
|---|---|
| Isopropyl myristate | 1.0 g |
| Maize oil | 2.0 g |
| Emulsifying surfactants | 6.0 g |
| Cetyl alcohol | 3.0 g |
| Stearic acid | 3.0 g |
| Titanium oxide nanoparticles | 0.5 g |
| Aqueous phase | |
| Thickener | 0.2 g |
| Preservative | 0.3 g |
| Fragrance | 0.4 g |
| Demineralized water | q.s. for 100 g |

Example 3

Emulsified Care Gel for the Skin

| Fatty phase | |
|---|---|
| Volatile silicone oil | 3.0 g |
| Purcellin oil | 7.0 g |
| Emulsifying surfactants | 0.3 g |
| Zinc oxide nanoparticles | 0.5 g |
| Aqueous phase | |
| Thickener | 0.6 g |
| Preservative | 0.3 g |
| Fragrance | 0.4 g |
| Ethyl alcohol | 10 g |
| Triethanolamine | 0.2 g |
| Demineralized water | q.s. for 100 g |

Example 4

Care Cream for the Skin

| Fatty phase | |
|---|---|
| Volatile silicone oil | 5.0 g |
| Liquid petrolatum | 10.0 g |
| Lanolin alcohol | 1.5 g |
| Emulsifying surfactants | 3.0 g |
| Cetyl alcohol | 0.5 g |
| Stearic acid | 0.72 g |
| Red iron oxide nanoparticles | 0.5 g |
| Aqueous phase | |
| Thickener | 0.3 g |
| Preservative | 0.16 g |
| Triethanolamine | 0.45 g |
| Demineralized water | q.s. for 100 g |

Example 5

Care Cream for the Skin

| Fatty phase | |
|---|---|
| Volatile silicone oil | 10.0 g |
| Liquid petrolatum | 5.0 g |
| Lanolin alcohol | 1.5 g |
| Emulsifying surfactants | 3.0 g |
| Cetyl alcohol | 0.5 g |
| Stearic acid | 0.72 g |
| Yellow iron oxide nanoparticles | 0.5 g |
| Aqueous phase | |
| Thickener | 0.3 g |
| Preservative | 1.16 g |
| NaOH | 0.45 g |
| Glycerol | 7.0 g |
| Demineralized water | q.s. for 100 g |

Example 6

Care Cream for the Skin

| Fatty phase | |
|---|---|
| Isopropyl myristate | 10.0 g |
| Silicone oil | 9.0 g |
| Emulsifying surfactant | 5.0 g |
| Cetyl alcohol | 9.0 g |
| Stearic acid | 1.0 g |
| Titanium oxide nanoparticles | 5.0 g |
| Aqueous phase | |
| Thickener | 0.5 g |
| Preservative | 0.3 g |
| Demineralized water | q.s. for 100 g |

Example 7

Care Cream for the Skin

| Fatty phase | |
|---|---|
| Volatile silicone oil | 10.0 g |
| Liquid petrolatum | 10.0.g |
| Maize oil | 4.0 g |

-continued

| | |
|---|---|
| Emulsifying surfactant | 2.3 g |
| Titanium oxide nanoparticles | 1.5 g |
| Aqueous phase | |
| Thickener | 0.4 g |
| Preservative | 0.3 g |
| Triethanolamine | 0.4 g |
| Demineralized water | q.s. for 100 g |

EXAMPLES 8 AND 9

Water-in-oil Emulsions

The following Examples 8 and 9 were obtained according to the following procedure:

The inorganic nanopigments were incorporated in the aqueous phase. The mixture was heated to 60–70° C. and was homogenized using a high-pressure homogenizer (500 bars pressure) of the Rannie type in one pass, and more if necessary. The fatty phase containing the emulsifying surfactants was heated to the same temperature in parallel, the fatty phase mixture was then incorporated with the aqueous phase and the emulsion was produced by stirring by shearing with a device of the Moritz type.

Example 8

Care Cream for the Skin

| | |
|---|---|
| Fatty phase | |
| Sunflower oil | 15.0 g |
| Liquid petrolatum | 10.0 g |
| Aromatic composition | 1.0 g |
| Emulsifying surfactant | 20 g |
| Aqueous phase | |
| Preservative | 0.3 g |
| Glycerol | 5.0 g |
| Magnesium sulphate | 0.5 g |
| Titanium oxide nanoparticles | 5.0 g |
| Demineralized water | q.s. for 100 g |

Example 9

Care Cream for the Skin

| | |
|---|---|
| Fatty phase | |
| Volatile silicone oil | 8.0 g |
| Liquid petrolatum | 5.0 g |
| Purcellin oil | 14.0 g |
| Isopropyl myristate | 5.0 g |
| Emulsifying surfactant | 5.4 g |
| Aqueous phase | |
| Sodium chloride | 0.5 g |
| Titanium oxide nanoparticles | 5.0 g |
| Preservative | 0.3 g |
| Demineralized water | q.s. for 100 g |

COMPARATIVE EXAMPLES

The mean diameter of the clusters of titanium nanooxide (fillers) formed during the dispersion of these pigments in a water-in-oil emulsion and in an oily single phase were measured.

First, a water-in-oil emulsion A based on the said pigments, which emulsion was obtained according to the process of the invention by means of a high-pressure homogenizer, was compared with a water-in-oil emulsion B based on the said pigments, which emulsion was obtained according to a conventional homogenization process.

Secondly, an oily single phase C based on the said pigments, which phase was obtained according to the process of the invention using a high-pressure homogenizer, was compared with an oily single phase D based on the said pigments, which phase was obtained according to a conventional homogenization process.

The mean diameter of the pigment clusters (expressed in nanometers) was measured for each composition A, B, C and D by means of a particle sizer of the Brookhaven Instrumentation type, reference BI 90 Particle Sizer.

The smaller the size of the diameters measured, the finer and more homogeneous the dispersion of the pigments.

| General formulation of the emulsions A and B | |
|---|---|
| Phase 1 | |
| Glycerol | 3 g |
| Demineralized water | q.s. |
| Phase 2 | |
| Emulsifying surfactant | 5 g |
| Stearyl alcohol | 1 g |
| Cetyl alcohol | 0.5 g |
| Cetearyl octanoate | 4 g |
| Liquid fraction of karite butter | 6 g |
| Silicone oil | 9 g |
| Preservative | 0.2 g |
| Titanium nanooxide | 5 g |
| Phase 3 | |
| Preservative | 0.3 g |
| Thickener | 1.2 g |
| Demineralized water | q.s. for 100 g |

| Procedure for the emulsions A and B | |
|---|---|
| Procedure for the emulsion A according to the invention | Procedure for the emulsion B according to the prior art |
| Phase 1 was heated to 70° C. | same |
| Phase 2 was heated to 65° C. and was left under conventional Rayneri-type stirring in order to wet the titanium nanooxide. | same |
| Phase 1 was poured into Phase 2 under conventional Rayneri-type stirring. | same |
| The mixture obtained was passed through the Rannie high-pressure homogenizer at 65° C. at 200 bars. | The mixture obtained was homogenized with stirring by shearing of the Moritz type. |
| The mixture was allowed to cool to room temperature and Phase 3 was added with stirring by shearing of the Moritz type. | same |

| General formulation of the oils C and D | |
|---|---|
| Phase 1 | |
| Stearyl alcohol | 1 g |
| Cetearyl octanoate | 24.5 g |
| Preservative | 0.2 g |
| Titanium nanooxide | 5 g |

-continued

Procedure for the oils C and D

| Procedure for the oil C according to the invention | Procedure for the oil D according to the prior art |
|---|---|
| Phase 1 was heated to 65° C. | same |
| The mixture was left under conventional Rayneri-type stirring in order to wet the titanium nanooxide. | same |
| The mixture obtained was passed through the Rannie high-pressure homogenizer at 65° C. at 200 bars. | The mixture obtained was homogenized with stirring by shearing of the Moritz type. |
| The mixture was allowed to cool to room temperature. | same |

The particle size results are shown in the following table:

| Formulation type | Dispersion with high-pressure homogenization | Conventional dispersion without high-pressure homogenization |
|---|---|---|
| Oil-in-water emulsion | A<br>537 nm | B<br>1532 nm |
| Oily single phase | C<br>3841 nm | D<br>4178 nm |

It was found that the titanium nanooxide particles were better dispersed in the formulations A and C, obtained according to the process of the invention using a high-pressure homogenizer, than in the formulations B and D, obtained according to a conventional process.

What is claimed is:

1. A process for the dispersion of a pulverulent filler selected from pulverulent organic fillers and pulverulent inorganic fillers in a vehicle comprising a fatty phase and an aqueous phase, wherein said process comprises at least one stage of mixing said pulverulent filler in said fatty phase by high-pressure homogenization prior to mixing with said aqueous phase.

2. A process according to claim 1, wherein said high-pressure homogenization is carried out at a pressure ranging from 100 to 800 bars.

3. A process according to claim 2, wherein said pressure ranges from 200 to 500 bars.

4. A process according to claim 1, wherein said stage of mixing is carried out at a temperature ranging from 20 to 85° C.

5. A process according to claim 4, wherein said temperature ranges from 25 to 70° C.

6. A process according to claim 1, wherein said fatty phase comprises at least one cosmetically or dermatologically acceptable compound selected from fatty substances, oils of vegetable, animal or mineral origin, and natural or synthetic waxes.

7. A process according to claim 1, wherein said vehicle is an oil-in-water or water-in-oil dispersion comprising a fatty phase and an aqueous phase.

8. A process according to claim 7, further comprising the steps of
   (1) predispersing said at least one pulverulent filler in a portion of said fatty phase of said oil-in-water or water-in-oil dispersion by high-pressure homogenization,
   (2) mixing said predispersed filler with the entire amount of said fatty phase, and
   (3) mixing said filler which has been mixed with said fatty phase with said aqueous phase.

9. A process according to claim 7, further comprising the steps of
   (1) predispersing said pulverulent filler in said fatty phase of said oil-in-water or water-in-oil dispersion by high-pressure homogenization and then (2) mixing said predispersed filler with said aqueous phase.

10. A process according to claim 1, wherein said pulverulent filler is selected from inorganic or organic pulverulent fillers of lamellar or spherical structure and mixtures thereof.

11. A process according to claim 10, wherein said pulverulent fillers of lamellar inorganic structure are selected from talcs, hydrated magnesium silicates, micas, aluminosilicates, clays, kaolin, hydrated aluminium silicate, boron nitrides and titanium oxide-coated micas.

12. A process according to claim 11, wherein said clays are sericites.

13. A process according to claim 10, wherein said pulverulent fillers of lamellar organic structure are selected from tetrafluoroethylene polymer powders and lauroyllysine.

14. A process according to claim 10, wherein said pulverulent fillers of spherical inorganic structure are selected from zinc and titanium oxides, precipitated calcium carbonate, magnesium carbonate and hydrogencarbonate, non-porous spherical silica, hydroxyapatite, silica microspheres with an open porosity or hollow silica microspheres, and glass or ceramic microcapsules.

15. A process according to claim 14, wherein said silica microspheres with an open porosity or said hollow silica microspheres are impregnated with a cosmetic active principle.

16. A process according to claim 10, wherein said pulverulent fillers of spherical organic structure are selected from metal soaps derived from organic carboxylic acids having from 8 to 22 carbon atoms; powders of non-expanded synthetic polymers; spheronized powders of crosslinked or non-crosslinked synthetic polymers; powders of organic materials of natural origin; and microporous polymer microspheres.

17. A process according to claim 16, wherein said microporous polymer microspheres are impregnated with at least one cosmetic active principle.

18. A process according to claim 16, wherein said pulverulent fillers of spherical organic structure can also be selected from crosslinked polymer microcapsules.

19. A process according to claim 16, wherein said metal soaps derived from organic carboxylic acids having from 8 to 22 carbon atoms are selected from zinc stearate, magnesium stearate, lithium stearate, zinc laurate and magnesium myristate.

20. A process according to claim 1, wherein said pulverulent filler is selected from organic coated pigments, inorganic coated pigments, organic non-coated pigments, inorganic non-coated pigments, nacreous pigments and mixtures thereof.

21. A process according to claim 20, wherein said pulverulent filler is selected from nanopigments based on coated or non-coated metal oxides.

22. A process according to claim 21, wherein said metal oxides are selected from titanium oxides, zinc oxides, iron oxides, zirconium oxides, cerium oxides or mixtures thereof.

23. A process according to claim 21, wherein said metal oxides have a mean primary particle size of 5 to 100 nm.

24. A process according to claim 23, wherein said mean primary particle size is from 10 to 50 nm.

25. A dispersion of at least one pulverulent filler selected from pulverulent organic fillers and pulverulent inorganic fillers in a vehicle comprising at least one fatty phase prepared by the process according to claim 1.

26. A cosmetic or dermatological composition in the form of a dispersion of at least one pulverulent filler selected from pulverulent organic fillers and pulverulent inorganic fillers in a vehicle composed of at least one fatty phase prepared by the process according to claim 1.

27. A composition according to claim 26, wherein said vehicle is an oil-in-water or water-in-oil dispersion comprising a fatty phase and an aqueous phase.

28. A composition according to claim 27, wherein said vehicle is an oil-in-water emulsion or a water-in-oil emulsion.

29. A composition according to claim 27, wherein said pulverulent filler is selected from inorganic or organic pulverulent fillers of lamellar or spherical structure which are compactable or difficult to compact and mixtures thereof.

30. A composition according to claim 29, wherein said pulverulent fillers of lamellar inorganic structure are selected from talcs, hydrated magnesium silicates, micas, aluminosilicates, clays, kaolin, hydrated aluminium silicate, boron nitrides and titanium oxide-coated micas.

31. A composition according to claim 30, wherein said clays are sericites.

32. A composition according to claim 29, in which said pulverulent fillers of lamellar organic structure are tetrafluoroethylene polymer powders or lauroyllysine.

33. A composition according to claim 29, wherein said pulverulent fillers of spherical inorganic structure are selected from zinc and titanium oxides, precipitated calcium carbonate, magnesium carbonate and hydrogencarbonate, non-porous spherical silica, hydroxyapatite, silica microspheres with an open porosity or hollow silica microspheres, and glass or ceramic microcapsules.

34. A composition according to claim 33, wherein said silica microspheres with an open porosity or said hollow silica microspheres are impregnated with a cosmetic active principle.

35. A composition according to claim 29, wherein said pulverulent fillers of spherical organic structure are selected from metal soaps derived from organic carboxylic acids having from 8 to 22 carbon atoms; powders of non-expanded synthetic polymers; spheronized powders of crosslinked or non-crosslinked synthetic polymers; powders of organic materials of natural origin; and microporous polymer microspheres.

36. A composition according to claim 35, wherein said microporous polymer microspheres are impregnated with at least one cosmetic active principle.

37. A composition according to claim 35, wherein said pulverulent fillers of spherical organic structure can also be selected from crosslinked polymer microcapsules.

38. A composition according to claim 35, wherein said metal soaps derived from organic carboxylic acids having from 8 to 22 carbon atoms are selected from zinc stearate, magnesium stearate, lithium stearate, zinc laurate and magnesium myristate.

39. A composition according to claim 26, wherein said pulverulent filler is selected from organic coated pigments, inorganic coated pigments, organic non-coated pigments, inorganic non-coated pigments, nacreous pigments and mixtures thereof.

40. A composition according to claim 39, wherein pulverulent filler is selected from nanopigments based on coated or non-coated metal oxides.

41. A composition according to claim 40, wherein said metal oxides are selected from titanium oxides, zinc oxides, iron oxides, zirconium oxides, cerium oxides and mixtures thereof.

42. A composition according to claim 40, wherein said metal oxides have a mean primary particle size ranging from 5 to 100 nm.

43. A composition according to claim 42, wherein said primary particle size is from 10 to 50 nm.

44. A composition according to claim 40, wherein said nanopigments based on metal oxides are selected from coated and non-coated titanium oxides.

45. A composition according to claim 44, wherein said titanium oxide is in the rutile, anatase or amorphous form.

46. A composition according to claim 26, comprising from 0.1 to 70% by weight of said at least one pulverulent filler with respect to the total weight of the composition.

47. A composition according to claim 26, further comprising at least one emulsifying agent.

48. A composition according to claim 47, wherein said emulsifying agent is present in an amount of from 0.5 to 40% by weight, with respect to the total weight of the composition.

49. A composition according to claim 48 wherein said emulsifying agent is present in an amount of from 2 to 15% by weight with respect to the total weight of the composition.

50. A composition according to claim 26, further comprising at least one adjuvant selected from ionic or non-ionic thickeners, conventional hydrophilic or lipophilic organic sunscreening agents which are active in the UV-A and/or the UV-B, softeners, antioxidants, opacifiers, stabilizers, emollients, moisturizing agents, vitamins, fragrances, preservatives, sequestering agents, dyes, and plasticizers.

51. A composition according to claim 26, wherein said vehicle is a water-in-oil emulsion comprising, with respect to the total weight of the composition:
(i) from 5 to 70% by weight of an aqueous phase, and
(ii) from 30 to 95% by weight of a fatty phase.

52. A composition according to claim 51, comprising from 10 to 50% by weight of said aqueous phase with respect to the total weight of the composition.

53. A composition according to claim 51, comprising from 40 to 85% by weight of said fatty phase with respect to the total weight of the composition.

54. A composition according to claim 26, wherein said vehicle is an oil-in-water emulsion comprising with respect to the total weight of the composition:
(i) from 5 to 95% by weight of an aqueous phase, and
(ii) from 1 to 50% by weight of a fatty phase.

55. A composition according to claim 54, comprising from 10 to 85% by weight of said aqueous phase with respect to the total weight of the composition.

56. A composition according to claim 54, comprising from 5 to 30% by weight of said fatty phase with respect to the total weight of the composition.

57. A process for preparing a care, make-up or hygiene product comprising incorporating a composition according to claim 27 as a base.

58. A process for preparing a product for reducing the harmful effects of ultraviolet radiation on the skin, scalp, nails, eyelashes, eyebrows or mucous membranes comprising incorporating a composition according to claim 26 as a base.

59. A process for the cosmetic treatment of the skin, hair, scalp, nails, eyelashes, eyebrows or mucous membranes, which comprises applying to said skin, hair, scalp, nails, eyelashes, eyebrows or mucous membranes a composition according to claim 26.

60. A process for reducing the harmful effects of ultraviolet radiation on the skin, scalp, nails, eyelashes, eyebrows or mucous membranes, which comprises applying to said skin, scalp, nails, eyelashes, eyebrows or mucous membranes a composition according to claim 26.

* * * * *

UNITED STATES PATENT AND TRADEMARK OFFICE
CERTIFICATE OF CORRECTION

PATENT NO.: 5,939,079
DATED: August 17, 1999
INVENTOR(S): Isabelle Le Royer et al.

It is certified that an error appears in the above-identified patent and that said Letters Patent is hereby corrected as shown below:

IN THE ABSTRACT:

Item [57], line 6, after "passes,", insert --and--.

IN THE CLAIMS:

Claim 40, col. 15, line 53, after "wherein", insert --said--.

Claim 57, col. 16, line 47, "claim 27" should read --claim 26--.

Signed and Sealed this

Twenty-eighth Day of December, 1999

*Attest:*

Q. TODD DICKINSON

*Attesting Officer*        *Acting Commissioner of Patents and Trademarks*